United States Patent

Angeletakis

[11] Patent Number: 6,020,395
[45] Date of Patent: Feb. 1, 2000

[54] HOMOGENEOUS MICROFILLED DENTAL COMPOSITE MATERIAL AND METHOD OF PREPARATION

[75] Inventor: Christos Angeletakis, Orange, Calif.

[73] Assignee: Kerr Corporation, Orange, Calif.

[21] Appl. No.: 09/003,307

[22] Filed: Jan. 6, 1998

[51] Int. Cl.[7] .............................. C08K 3/34; A61K 6/08
[52] U.S. Cl. .................. 523/116; 523/115; 523/212; 524/264; 524/492; 524/493; 524/494; 428/405
[58] Field of Search ..................... 523/115, 116, 523/212; 524/264, 493; 428/405

[56] References Cited

U.S. PATENT DOCUMENTS

| | | | |
|---|---|---|---|
| 4,044,044 | 8/1977 | Saito | 260/47 |
| 4,389,497 | 6/1983 | Schmit et al. | 523/116 |
| 4,427,799 | 1/1984 | Orlowski et al. | 523/212 |
| 4,617,327 | 10/1986 | Podszun | 523/116 |
| 4,781,940 | 11/1988 | Denton, Jr. | 427/2 |
| 4,970,245 | 11/1990 | Futami et al. | 523/109 |
| 5,055,497 | 10/1991 | Okada et al. | 523/116 |
| 5,116,885 | 5/1992 | Hattori et al. | 523/200 |
| 5,183,834 | 2/1993 | Gorlich et al. | 523/105 |
| 5,350,782 | 9/1994 | Sasaki et al. | 523/116 |
| 5,354,785 | 10/1994 | Rheinberger et al. | 523/116 |
| 5,548,000 | 8/1996 | Nagel et al. | 523/115 |
| 5,707,440 | 1/1998 | Hengchang et al. | 428/403 |

*Primary Examiner*—Andrew E. G. Merriam
*Attorney, Agent, or Firm*—Wood, Herron & Evans, L.L.P.

[57] ABSTRACT

A homogeneous microfilled dental composite material comprised of a mixture of polymerizable monomers and an inorganic filler, wherein said filler is comprised of silane treated fused silica aggregates having a size ranging from submicron to about 160 $\mu$m. The aggregates are comprised of agglomerates of fumed silica having an average agglomerate size in the range of approximately 0.5 to 50 $\mu$m, and the agglomerates are comprised of primary particles of fumed silica having an average particle size in the range of approximately 1 to 100 nm. The primary particles are interconnected by siloxane bridges formed by burning an organosilane coating on the fumed silica.

23 Claims, No Drawings

HOMOGENEOUS MICROFILLED DENTAL COMPOSITE MATERIAL AND METHOD OF PREPARATION

BACKGROUND OF THE INVENTION

This invention relates to a homogeneous microfill composite material for use in dental restorations and for layering over microhybrids.

Microfill composite materials are generally produced by mixing finely divided silica with a polymerizable monomer, usually an acrylate or methacrylate-based resin, heat polymerizing the mixture in bulk, and pulverizing the mixture down to the desired agglomerate size to give a filler material comprised of splintered polymerized particles. This filler material is then mixed with a polymerizable monomer, again typically an acrylate or methacrylate-based resin, and an additional filler material, such as a colloidal silica. Thus, there are typically two polymerization steps, with the first being referred to as prepolymerization.

For example, U.S. Pat. No. 4,781,940 describes a process for producing a dental composite material using a prepolymerization step. A slurry of silica in a polymerizable monomer/solvent solution is prepared, followed by evaporating the solvent by heating at atmospheric pressure. The monomer coated silica particles are individualized by sieving, then polymerized by heating, and again sieved. No pulverization step is required. This filler material is then mixed with an additional filler and a resin, which may have the same monomers as those used in the monomer/solvent solution.

The composite material resulting from processes such as that of U.S. Pat. No. 4,781,940 is heterogeneous as a result of the prepolymerization step. Heterogeneous dental fillers are hydrolytically unstable and suffer from catastrophic marginal failures when used in dental restorations, in part, as a result of separation along the prepolymerized particle-resin matrix interface caused by percolation of aqueous fluids. Thus, it is desirable to develop a microfill that does not involve prepolymerization of the silica particles.

U.S. Pat. No. 4,389,497 is directed to a filler material which may or may not include a prepolymerization step, and therefore, may be heterogeneous or homogeneous. The inorganic filler material used is in the form of agglomerates of silicic acid, which can be produced with or without a binding agent. For example, the agglomerates could be formed by premixing silicic acid with a water glass solution, a boric acid solution, or an alcoholic aluminum alcoholate solution. The agglomerated material is then adjusted to the desired size by milling and screening. A further manner of production involves premixing the silicic acid with organosilicon compounds preferably containing a polymerizable residue and a polymerization catalyst if necessary, followed by heat polymerization. The organic constituents are then burned and the mixture is brought up to more than 600° C. Agglomerate reduction to the desired size is then achieved by milling and screening, subsequent to the heating step.

In addition to the homogeneous composites disclosed in U.S. Pat. No. 4,389,497, there are other homogeneous composites that have been offered commercially. These homogeneous composites have proved unsuccessful in that they are difficult to prepare reproducibly and the Theological properties are difficult to control. This is due to difficulty in controlling the agglomeration of silica particles. Thus, it is desirable to develop a process in which the agglomeration can be controlled to prepare reproducibly a homogeneous microfill composite material.

SUMMARY OF THE INVENTION

The present invention provides a hydrolytically stable, homogeneous microfilled dental composite material comprised of a polymerizable monomer mixed with bridged silica particles for use in dental restorations, and a method for making the same, such that the material is easy to prepare reproducibly and the Theological properties of the material are controllable. To this end, and in accordance with the principles of the present invention, raw fumed silica is coated with silane, dried, milled to a fine particle size, and heated to burn the silane coating. Siloxane units are thereby formed, which bridge together the fumed silica aggregates to produce an interconnected sponge-like mass, allowing for interpenetration of resin, without the need for a prepolymerization step. The bridged silica particles are then treated with silane, which has the advantage of reducing water percolation. The homogeneous resin matrix of the present invention leads to higher mechanical properties, such as flexural strength and toughness, and reduced crack propagation, thus reducing the chance of catastrophic marginal failure in dental restorative applications, as well as reducing gouging during finishing. A further advantage of the present invention is that the composite material is highly polishable and can be brought rapidly to a high luster, which is essential for materials used in exterior tooth applications. Furthermore, this high luster is retained after tooth brushing and chewing. Thus, there is provided a highly polishable, hydrolytically stable, homogeneous microfilled dental composite material with excellent mechanical properties for use in dental restoration.

DETAILED DESCRIPTION

The filler material is comprised mainly of fumed (pyrogenic) silica. Raw fumed silica, such as OX-50 commercially available from Degussa Corp., Ridgefield Park, N.J., contains primary particles substantially spherical in shape, ranging in size from 1–100 nm with an average size of 40 nm. OX-50 has a high purity and is of appropriate size, which is important for obtaining optimal results according to the teachings of the present invention. These primary particles are bound together to form agglomerates, ranging in size from about 0.5 to 50 $\mu$m. These agglomerates become physically entangled, forming aggregates.

To produce a uniform raw material for subsequent processing, a deagglomeration step may be performed in which 30–70% by volume raw fumed silica is combined with water and mixed in a colloid mill. For example, 50% by volume fumed silica is mixed with 50% by volume water and mixed in a batch-type Cavimix™, available from Arde Barmco Inc., Norwood, N.J. The resulting slurry is dried, milled, such as by hammer milling, dry-ball milling or impact pulverizer milling, and sieved to produce aggregates with a maximum size of 160 $\mu$m, such as by sieving through 80–95 mesh. The use of a colloid mill greatly increases the cost of the operation. Thus, this deagglomeration step is preferably omitted by exercising greater control in the subsequent processing steps.

The uniform raw fumed silica is coated with approximately 20% by volume organosilane, such as A-174 ($\gamma$-methacryloxypropyltrimethoxysilane) available commercially from Union Carbide, Danbury, Conn. This is accomplished in a V-blender, for example, using an aqueous solution spray. The product is then dried, such as in a forced air oven. The temperature and drying time are not critical. Rather, the drying is carried out so as to drive off any excess water from the material. For example, drying in a forced air oven at approximately 110° C. for about 24 hours is sufficient for the purpose.

The silane-coated silica is milled, such as by passing the material through a hammer mill, dry-ball mill or impact pulverizer mill, in order to generate particles ranging in size from submicron up to about 80 μm, with an average aggregate size of 10 μm. The silane coated fumed silica is then heated in a room atmosphere to a temperature in the range of about 800–1100° C. for 1 to 15 hours. The organic portion of the silane is thereby burned generating the following products:

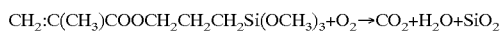

The SiO$_2$ formed has a tendency to associate with itself, thereby forming siloxane units (Si—O). These siloxane units can bridge together the fumed silica, resulting in an interconnected sponge-like mass, referred to as fused fumed silica. The agglomerate reduction step, having been carried out prior to heating of the silica, provided greater control over the subsequent agglomeration of the bridged silica particles.

The fused fumed silica is then surface treated with an organosilane to produce a hydrophobic material, such as by coating with A-174 using an aqueous spray in a V-blender, followed by drying in room atmosphere using a two temperature cycle. For example, the silane-coated fused fumed silica is dried at approximately 110° C. for 1–4 hours, then at approximately 50° C. for 15–20 hours. The product is then sieved to produce an average aggregate size of about 10 μm, with a range from submicron up to about 160 μm, such as by sieving through 80–95 mesh. The filler, silane-treated fused fumed silica, is ready to be compounded in paste.

A homogeneous resin mixture consisting of a polymerizable organic acrylic monomer is prepared for mixing with the filler. For example, the following components (in parts by weight) may be mixed together to give a preferred homogeneous resin mix:

60–90 parts Diurethane Dimethacrylate (Rohamere 6661-0, Huls America, Inc. Piscataway, N.J.)

10–40 parts Triethyleneglycoldimethacrylate 0.4–1.0 parts 2-Hydroxy-4-methoxybenzophenone 0.07–0.4 parts Camphorquinone 0.1–1.0 parts p-octyl dimethylamino-benzoate.

This cured resin system is tough and highly cross-linked. The goal in selecting a resin system is to provide a resin with a refractive index similar to that of silica, such that they are a relatively good match from a visual and aesthetic standpoint.

The filler is then dispersed in resin with additional fumed silica, such as silicone treated fumed silica (Aerosil 200, available commercially from Degussa Corp.) by mixing together until uniform, approximately 3–10 hours, such as by mixing in a planetary mixer. The components are mixed in the following amounts:

45–58 wt. % Filler

2–7 wt. % Silicone-treated fumed silica (Aerosil 200, Degussa)

40–48 wt. % Resin.

A deaeration step is then carried out for at least 10 minutes, by which excess air in the composite paste material is eliminated by bubbling the air out in a vacuum. Deaerating is advantageously done in an attenuated oxygen atmosphere.

The microfill of the present invention exhibits better physical properties than the currently marketed microfills as a result of the combination of agglomerate reduction prior to heating the fumed silica particles, the silane treatment of the fused silica, and the use of fumed silica bridged by siloxane units. For example, substantially higher flexural strength and toughness are obtained with the present invention. This assures higher fracture resistance than a typical microfill. This high strength and fracture resistance help reduce gouging during finishing. Better hydrolytic stability from reduced water percolation at the filler-resin matrix interface, higher mechanical properties and reduced crack propagation even in feathered edges are expected due to the silane treatment and the absence of prepolymerized particles. The unique, complex morphology of the bridged silica particles presents a higher surface area than the original silica, allowing for intimate resin-filler particle interactions. A further benefit of the present invention is reduced wear due to the complexity of the bridged silica particles-resin matrix interface. The fragile nature of this filler material results in the exposed filler particles shearing off rather than exfoliating during wear.

Together, these improvements are expected to lead to better long term clinical performance, with the problem of catastrophic marginal failure, as observed with heterogeneous microfills, considerably lessened. Furthermore, the process of the present invention allows for control of the rheological properties due to easier control of the agglomerate of fumed silica by agglomerate reduction prior to heat treating the silica. Moreover, the homogeneous microfill of the present invention is simpler to prepare reproducibly than the heterogeneous and homogeneous microfills of the prior art. Esthetic concerns are met in that the present process results in a material that is highly translucent, polishable and can be brought rapidly to a high luster that is retained after brushing and chewing.

EXAMPLE 1

Raw OX-50 was coated with 20% by weight A-174 organosilane in a V-blender using an aqueous solution spray, dried in a forced air oven at 100° C. for 24 hours, and hammermilled to a 10 μm average particle size. The silane-coated OX-50 was oxidized at 1050° C. for 4 hours, resulting in bridged silica particles (fused silica). The fused silica was then surface treated with 7% by weight A-174 organosilane in a V-blender using an aqueous solution spray. The silane-treated fused silica was dried at 110° C. for 3 hours and at 55° C. for 16 hours, then sieved through 95 mesh. The resulting filler consisted of agglomerates of Si—O bridged 0.04 μm fumed silica with aggregates of 10 μm mean size and a range of from submicron to 160 μm. The following components (in parts by weight) were mixed together and stirred for a few hours to give a homogeneous resin mix:

80.00 parts Diurethane Dimethacrylate (Rohamere 6661-0)

20.00 parts Triethyleneglycoldimethacrylate 0.80 parts 2-Hydroxy-4-methoxybenzophenone 0.12 parts Camphorquinone 0.60 parts p-octyl dimethylamino-benzoate.

The following components were mixed in a planetary mixer until uniform (approximately 8 hours) followed by deaeration in an attenuated oxygen atmosphere:

50 wt. % filler 45 wt. % resin 5 wt. % silicone treated Aerosil 200 fumed silica (Degussa Corp.)

Table 1 provides the physical properties of the resulting homogeneous microfill, as compared to current heterogeneous microfills marketed by various companies.

TABLE 1

|  | Invention | Heliomolar (Vivadent) | Silux Plus (3M) | Durafil (Kulzer) | Renamel (Cosmodent) |
|---|---|---|---|---|---|
| Flexural Strength, FS (MPa)* | 110 (11) | 92 (13) | 79 (10) | 83 (12) | 80 (9) |
| Flexural Modulus, FM (MPa)* | 6,400 (374) | 6,277 (388) | 7,000 (639) | 5,325 (301) | 5316 (250) |
| Flexural Toughness (FS$^2$/2FM) | 0.95 | 0.67 | 0.45 | 0.65 | 0.60 |
| Compressive Strength* (MPa) | 391 (23) | 279 (81) | 248 (96) | 428 (47) | 383 (31) |
| Rockwell Hardness (15T scale) | 79.2 | 77.0 | 81.7 | 76.9 | 78.5 |
| Consistency-Slump (cm) | 2.6 | 2.7 | 4.3 | 2.7 | 2.7 |
| % Translucency (1.0 mm) | 25.5 | 19.1 | 22.5 | 22.3 | 24.6 |
| Water Sorption* (mg/cm$^2$) | 0.66 | 0.59 | — | 0.66 | — |
| Water Solubility* (mg/cm$^2$) | 0 | 0 | — | 0.04 | — |

*Testing done in accordance with standard ISO testing protocols.
( ) Standard deviation While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the raw material may be any commercially available brand of fumed silica with a high purity and approximate average particle size of 40 nm. Furthermore, variations in time and temperatures may result in a homogeneous microfill within the spirit of the present invention. The invention in its broader aspects is therefore not limited to the specific details, representative method and example described. Accordingly, departures may be made from such details without departing from the scope or spirit of applicant's general inventive concept.

What is claimed is:

1. A method for preparing dental composite material comprising the steps of:
    coating a raw material consisting of aggregates of fumed silica with an organosilane to form a silane-coated fumed silica;
    drying the silane-coated fumed silica;
    reducing the silane-coated fumed silica to an aggregate size of about 80 μm or less, and an average aggregate size of about 10 μm;
    oxidizing the organic portion of the organosilane to form fused silica;
    treating the fused silica with an organosilane to form a silane-treated fused silica;
    drying the silane-treated fused silica, followed by sieving; and
    combining a resin consisting of a polymerizable monomer, the silane-treated fused silica, and an additional fumed silica to form a composite material.

2. The method of claim 1, wherein the raw material is first combined with water and mixed in a colloid mill to form a slurry, which is then dried, milled, and sieved through 80–95 mesh, thereby creating a uniform raw material.

3. The method of claim 1, wherein the aggregates of fumed silica have an average particle size of about 40 nm.

4. The method of claim 1, wherein the organosilane is γ-methacryloxypropyltrimethoxysilane.

5. The method of claim 1, wherein the coating and treatment with an organosilane is accomplished in a V-blender using an aqueous solution spray.

6. The method of claim 5, wherein the aqueous solution spray is comprised of approximately 20% by weight silane or less.

7. The method of claim 1, wherein the drying of the silane-coated fumed silica is accomplished in a forced air oven.

8. The method of claim 1, wherein the silane-coated fumed silica is reduced by hammer milling, dry ball milling or impact pulverizer milling.

9. The method of claim 1, wherein the oxidizing is accomplished by heating to a temperature between about 800° C. and 1100° C.

10. The method of claim 1, wherein drying of the silane-treated fused silica is accomplished by a two-temperature drying cycle.

11. The method of claim 10, wherein the two-temperature drying cycle consists of drying at approximately 110° C. for about 1–4 hours and at approximately 55° C. for about 15–20 hours.

12. The method of claim 1, wherein the sieving is accomplished through 80 to 95 mesh.

13. The method of claim 1, wherein the polymerizable monomer is an acrylic monomer.

14. The method of claim 1, wherein the resin consists of 60–90 parts by weight of Diurethane Dimethacrylate, 10–40 parts by weight Triethyleneglycoldimethacrylate, 0.4–1.0 part by weight 2-Hydroxy-4-methoxybenzophenone, 0.07–0.4 part by weight Camphorquinone, and 0.1–1.0 part by weight p-octyl dimethylamino-benzoate.

15. The method of claim 1, wherein the composite material contains about 2–7 wt. % fumed silica, 45–58 wt. % silane-treated fused silica, and 40–48 wt. % resin.

16. The method of claim 1, wherein the additional fumed silica is a silicone-treated fumed silica.

17. The method of claim 1, wherein the combined resin, silane-treated fused silica and additional fumed silica are mixed until uniform in a planetary mixer.

18. The method of claim 17, wherein the combined resin, silane-treated fused silica and additional fumed silica are mixed for about 3 to 10 hours.

19. The method of claim 1, wherein the composite material is deaerated.

20. The method of claim 19, wherein the deaeration is accomplished in an oxygen atmosphere.

21. A method for preparing dental composite material comprising the steps of:
    coating a raw material consisting of aggregates of fumed silica with an aqueous solution containing approximately 20% by weight organosilane to form a silane-coated fumed silica, wherein the aggregates of fumed silica have a particle size of 1–100 nm;
    drying the silane-coated fumed silica in a forced air oven;
    milling the silane-coated fumed silica to generate particles with an aggregate size of about 80 μm or less, and an average aggregate size of about 10 μm;
    heating the silane coated fumed silica to between about 800 and 1100° C. thereby burning the organic portion of the organosilane to form fused silica;

treating the fused silica with an aqueous solution containing approximately 7% by weight organosilane to form a silane-treated fused silica;

drying the silane-treated fused silica at approximately 110° C. for about 1–4 hours and at approximately 55° C. for about 15–20 hours, followed by sieving;

combining resin consisting of 60–90 parts by weight of Diurethane Dimethacrylate, 10–40 parts by weight Triethyleneglycoldimethacrylate, 0.4–1.0 part by weight 2-Hydroxy-4-methoxybenzophenone, 0.07–0.4 part by weight Camphorquinone, and 0.1–1.0 part by weight p-octyl dimethylamino-benzoate with the silane-treated fused silica and a silicone treated fumed silica to form a composite material; and deaerating the composite material in an oxygen atmosphere.

22. A method of restoring a tooth comprising the steps of:

preparing the tooth for restoration; and applying to the prepared tooth a dental restorative composite prepared according to the process of claim 1.

23. A method of restoring a tooth comprising the steps of:

preparing the tooth for restoration; and applying to the prepared tooth a dental restorative composite prepared according to the process of claim 21.

* * * * *

UNITED STATES PATENT AND TRADEMARK OFFICE
CERTIFICATE OF CORRECTION

PATENT NO : 6,020,395
DATED : February 1, 2000
INVENTOR(S) : Christos Angeletakis It is certified that error appears in the above-identified patent and that said Letters Patent are hereby corrected as shown below:

In column 1, line 62, delete "Theological", and insert therefor --Rheological--.

In column 2, line 7, delete "Theological", and insert therefor --Rheological--.

In column 2, line 60, delete "by volume", and insert therefor --by weight--.

Signed and Sealed this

Eighth Day of May, 2001

Attest:

NICHOLAS P. GODICI

Attesting Officer

Acting Director of the United States Patent and Trademark Office